(12) United States Patent
Saeed et al.

(10) Patent No.: US 10,093,667 B1
(45) Date of Patent: Oct. 9, 2018

(54) COUMARINYL-THIAZOLE-SULFONYL CONJUGATE AND PREPARATION THEREOF

(71) Applicants: COMSATS Institute of Information Technology, Abbottabad (PK); Quaid-I-Azam University, Islamabad (PK)

(72) Inventors: Aamer Saeed, Islamabad (PK); Khalid Rauf, Abbottabad (PK); Yasser M S A Alkahraman, Abbottabad (PK)

(73) Assignees: COMSATS Institute of Information Technology, Abbottabad (PK); Quaid-I-Azam University, Islamabad (PK)

( * ) Notice: Subject to any disclaimer, the term of this patent is extended or adjusted under 35 U.S.C. 154(b) by 0 days.

(21) Appl. No.: 15/783,783

(22) Filed: Oct. 13, 2017

(30) Foreign Application Priority Data

May 24, 2017 (PK) ..................... 296/2017

(51) Int. Cl.
 *C07D 417/14* (2006.01)
 *A61K 31/427* (2006.01)
(52) U.S. Cl.
 CPC .......... *C07D 417/14* (2013.01); *A61K 31/427* (2013.01)
(58) Field of Classification Search
 CPC .............................. C07D 417/14; A61K 31/427
 See application file for complete search history.

(56) References Cited

PUBLICATIONS

Abdelhamid, 2008, J. Heterocycli Chem, vol. 45, p. 1719-1728. (Year: 2008).*
Xu, 2015, Asia-Pacific Energy Equipment Engineering Research Conference, p. 135-138. (Year: 2015).*
Hyman, 2008, Nature, vol. 455, p. 890-893. (Year: 2008).*

* cited by examiner

*Primary Examiner* — Rebecca L Anderson
*Assistant Examiner* — Karen Cheng
(74) *Attorney, Agent, or Firm* — H.C. Park & Associates, PLC

(57) ABSTRACT

The present application relates to a compound of formula (I)

The present application also relates to synthesizing the compound of formula I and treating a patient with the compound of formula I having a neuropsychiatric illnesses such as a depressive disorder, schizophrenia; alcohol, nicotine, and morphine withdrawal induced depression and hyperalgesia; neuropathic pain caused by anticancerous drugs; diabetic neuropathic pain; obsessive compulsive disorder; alcohol withdrawal syndrome; static and dynamic allodynia in diabetic and cancer patients on anticancer therapy and chronic pain therapy.

6 Claims, No Drawings

COUMARINYL-THIAZOLE-SULFONYL CONJUGATE AND PREPARATION THEREOF

CROSS-REFERENCE TO RELATED APPLICATION

This application claims priority from and the benefit of Pakistani Patent Application No. 296/2017, filed on May 24, 2017, which is hereby incorporated by reference for all purposes as if fully set forth herein.

BACKGROUND

Field

Exemplary embodiments relate to compounds, compositions, and methods that treat neuropsychiatric illnesses.

Discussion of the Background

Literature is inundated with the synthesis and bioactivity of coumarin derivatives. Installation of thiazole nucleus to coumarins leads to further enhancement of bioactivities, especially for anti-inflammatory, analgesic, antimicrobial, anti-HIV, antihypertensive, and herbicidal activity.

Sulfamethoxazole is used for bacterial infections, for example, urinary tract infections, bronchitis, and prostatitis and is successful against both gram negative and positive bacteria such as *Listeria monocytogenes* and *E. coli*. Chemically, it is a sulfonamide derivative and prevents folic acid synthesis in the bacteria that must synthesize their own folic acid.

Linkage of Sulfamethoxazole gives additional improvement in the in the biological activities of these molecules.

In general attachment of 4-amionosulphamyl/sulfonyl further increase the biological diversity.

The sulfonyl group can be further be connected with alkyl, heteroaryl or aryl substituents which can further augment the effectiveness.

Thus, in these molecules there are at least three points of introducing diversity: coumarin nucleus, thiazole ring as well as the sulfonyl moiety.

The above information disclosed in this Background section is only for enhancement of understanding of the background of the inventive concepts, and, therefore, it may contain information that does not form the prior art that is already known in this country to a person of ordinary skill in the art.

SUMMARY

Exemplary embodiments provide compounds, compositions, and method of making the compounds that treat neuropsychiatric illnesses.

Additional aspects will be set forth in the detailed description which follows, and in part, will be apparent from the disclosure, or may be learned by practice of the inventive concepts.

Exemplary embodiments include a compound having a structure of formula (I):

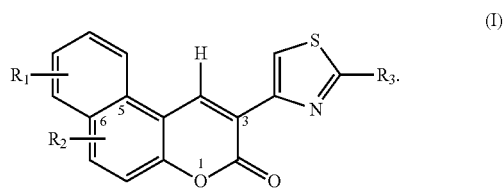

$R_1$ is selected from the group consisting of H, alkyl (C1-C17), X, $NO_2$, and CN. $R_2$ is selected from the group consisting of H, alkyl (C1-C17), X, $NO_2$, and CN. $R_3$ is selected from the group consisting of:

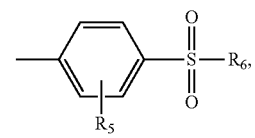

(R₃-1)

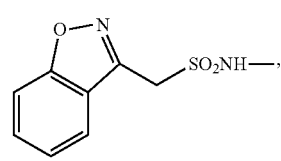

(R₃-2)

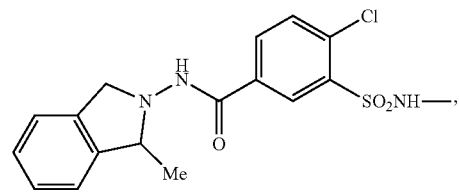

(R₃-3)

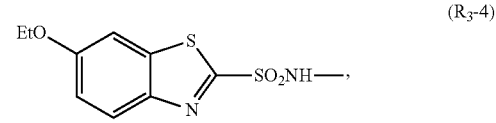

(R₃-4)

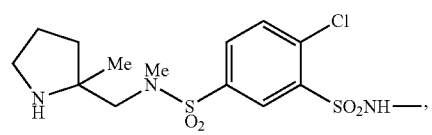

(R₃-5)

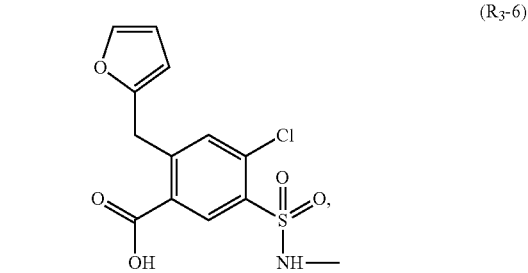

(R₃-6)

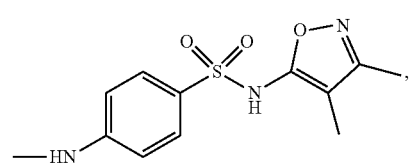

(R₃-7)

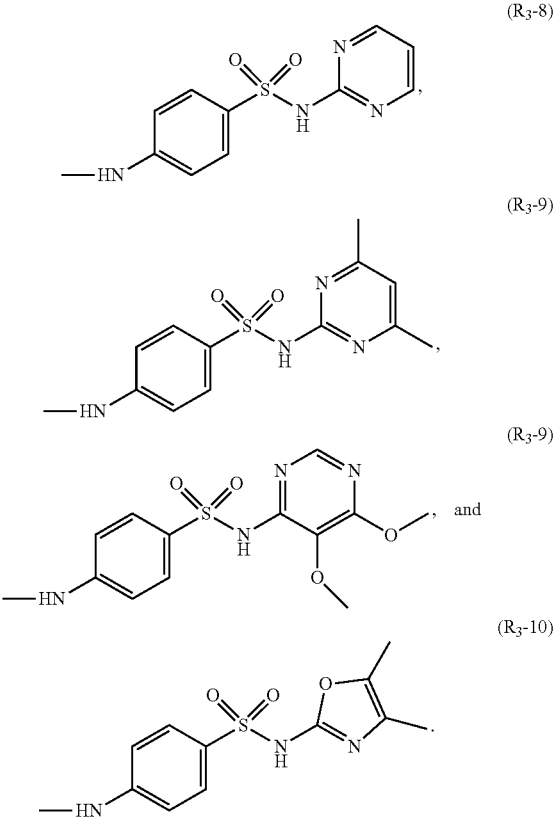

$R_5$ is selected from the group consisting of $NH_2$, NH-alkyl, NH-aryl, NH-heteroaryl, X, $NO_2$, and CN. $R_6$ is selected from the group consisting of $NH_2$, NH-alkyl, NH-aryl, NH-heteroaryl, X, $NO_2$, CN, —$CH_2$Ph-substitued phenyl, and heteroaryl alkyl (C1-C17). X is a halogen. In addition, the compound may be a derivative of formula (I) or a pharmaceutically acceptable salt of the formula (I) or derivative.

The compound may have the structure of formula (Ia)

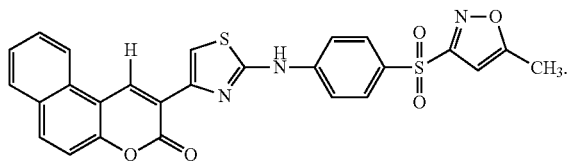

(Ia)

In addition, the compound may be a derivative of formula (Ia) or a pharmaceutically acceptable salt of formula (Ia) or the derivative.

Exemplary embodiments include a method to prepare a compound having the structure of formula (I), a derivative of formula (I), or a pharmaceutically acceptable salt thereof. The method includes adding piperidine to a cold stirred mixture of suitably substituted ortho-hydroxybenzalaldehyde or ortho-hydroxynaphthaldehyde and alkyl acetoacetate, filtering first solids after a 30-minute time period, washing the first solids with cold ethanol, crystallizing the first solids to obtain a substituted 2-acetylchromen-3-ones, adding a solution of bromine dissolved in chloroform to a solution of 2-acetyl-3H-benzo[f]chromen-3-one dissolved in chloroform to form a mixture, refluxing the mixture for 2 hours, cooling the mixture, separating second solids and crystallizing from chloroform-ethanol to get suitably substituted 2-(2-bromoacetyl)-chromen-3-ones, preparing a solution of the suitably substituted 2-(2-bromoacetyl)-chromen-3-ones and ethanol, adding potassium thiocyanate to the solution in small portions to form a mixture, stirring the reaction mixture at 45-50° C. for one hour, adding, to the mixture, suitably substituted amino containing compound, refluxing the reaction mixture for 5 hours, pouring the reaction mixture into ice-cold water to separate third solids, and purifying the third solids by recrystallization from ethanol to obtain compound of formula (I).

Exemplary embodiments include a method to prepare a compound having the structure of formula (Ia), a derivative of formula (Ia), or a pharmaceutically acceptable salt thereof. The method includes preparing a mixture of 2-hydroxy-1-naphthalaldehyde and ethyl acetoacetate, adding piperidine to the cold stirred mixture, filtering first solids after a 30-minute time period, washing the first solids with ethanol, crystallizing the first solids from pure water to get 2-acetyl-3H-benzo[f]chromen-3-one, adding a solution of bromine and chloroform into another solution of 2-acetyl-3H-benzo[f]chromen-3-one and chloroform to form a mixture, heating the mixture under reflux for 2 hours, cooling the mixture, separating second solids and crystallizing from chloroform-ethanol to get pure 2-(2-bromoacetyl)-3H-benzo[f]chromen-3-one, preparing a solution of the 2-(2-bromoacetyl)-3H-benzo[f]chromen-3-one in ethanol, adding potassium thiocyanate to the solution in small portions to form the mixture, stirring the reaction mixture 45-50° C. for one hour, adding 4-((5-methylisoxazol-3-yl)sulfonyl)aniline) (Sulfamethoxazole) to the mixture, refluxing the reaction mixture 5 hours, pouring the mixture into ice-cold water to get third solids, purifying the third solids by recrystallization from ethanol to obtain the compound of formula (Ia).

Exemplary embodiments include a method of treating a neuropsychiatric illness in a patient. The method includes administering to a patient in need thereof a therapeutically effective amount of a compound of claim 1, or a derivative thereof, or a pharmaceutically acceptable salt of the compound or the derivative.

The neuropsychiatric illness may be selected from the group consisting of depressive disorders; schizophrenia; alcohol, nicotine, and morphine withdrawal induced depression and hyperalgesia; neuropathic pain caused by anticancerous drugs; diabetic neuropathic pain; obsessive compulsive disorder; alcohol withdrawal syndrome; and static and dynamic allodynia in diabetic and cancer patients on anticancer therapy and chronic pain therapy.

Exemplary embodiments include a pharmaceutical composition including a therapeutically effective amount of a compound of formula (I), or a derivative thereof, or a pharmaceutically acceptable salt of the compound or derivative and a pharmaceutically acceptable carrier.

Exemplary embodiments include a method of treating a neuropsychiatric illness in a patient. The method includes administering to a patient in need thereof a therapeutically effective amount of the compound of formula (Ia), or a derivative thereof, or a pharmaceutically acceptable salt of the compound or the derivative.

The neuropsychiatric illness may be selected from the group consisting of depressive disorders; schizophrenia; alcohol, nicotine, and morphine withdrawal induced depression and hyperalgesia; neuropathic pain caused by anticancerous drugs; diabetic neuropathic pain; obsessive compulsive disorder; alcohol withdrawal syndrome; and static and dynamic allodynia in diabetic and cancer patients on anti-cancer therapy and chronic pain therapy.

Exemplary embodiments include a pharmaceutical composition including a therapeutically effective amount of a compound of formula (Ia) or a derivative thereof, or a pharmaceutically acceptable salt of the compound or derivative and a pharmaceutically acceptable carrier.

Additional features of the inventive concepts will be set forth in the description which follows, and in part will be apparent from the description, or may be learned by practice of the inventive concepts.

DETAILED DESCRIPTION

Exemplary embodiments of the present invention provide a compound which as a drug is a potential candidate for neuropsychiatric illnesses, specifically depression. The drug is also effective for the management of depression associated with alcohol addiction and withdrawal. The drug has also been found to be effective in the depression found in bipolar disorders patients and schizophrenic patients. The drug has considerable safety and efficacy and has been found to be effective in the treatment of neuropathic pains, with or without diabetes, and in the management of Vincristine induced neuropathies. The drug has also shown a safe and strong ameliorating effect in treating depression associated with nicotine and morphine dependence. The drug has a strong potential to modulate emotions positively and improves socialization in various stressed and pain models, so can be considered a potential candidate for the treatment of refractive depression in patients with suicidal tendencies, and self-harm profile.

The drug also can be used to prevent alcohol addiction relapse after successful detoxification. The drugs are well absorbed orally and can be given orally and parenterally. The drugs are safe in long term use and haven't shown any carcinogenic profile.

The drug also alleviates generalized body aches (a neuropsychiatric illness) associated with drug addiction like alcohol, morphine, and nicotine. The drug is also safe and is a candidate for the management of Tourette syndrome (a genetic neuropsychiatric illness) in children.

The drug is also a potential candidate for the management of alcohol addiction, dependence, withdrawal induced anxiety and depression, and withdrawal induced hyperalgesia.

Exemplary embodiments include a compound have the structure of formula (I)

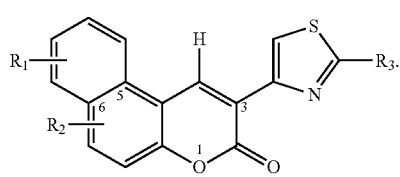

(I)

In formula (I), $R_1$ and $R_2$ are independently one selected from the group consisting of H, alkyl (C1-C17), X, NO2, and CN. R3 is selected from the group consisting of:

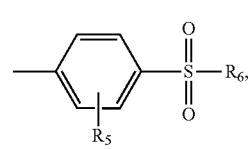

(R₃-1)

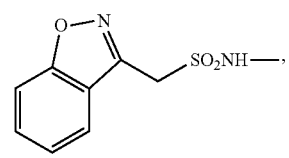

(R₃-2)

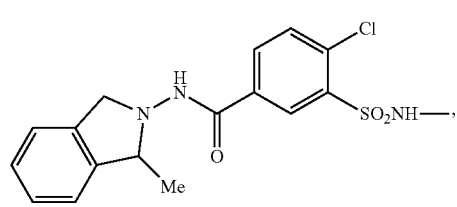

(R₃-3)

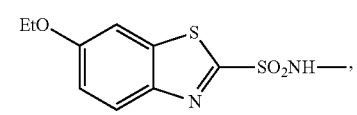

(R₃-4)

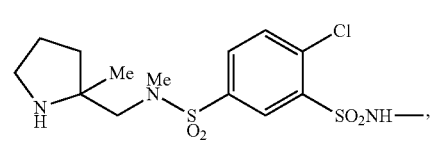

(R₃-5)

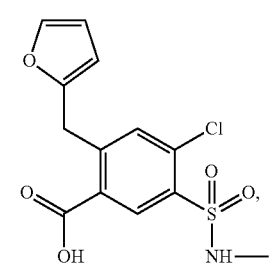

(R₃-6)

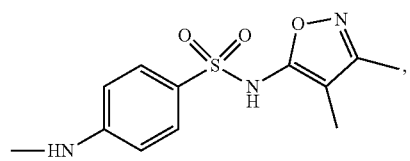

(R₃-7)

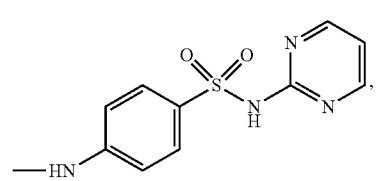

(R₃-8)

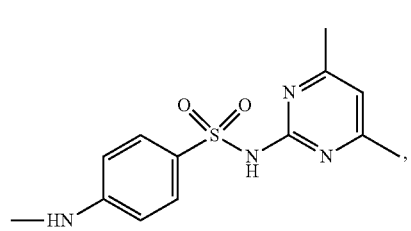

(R₃-9)

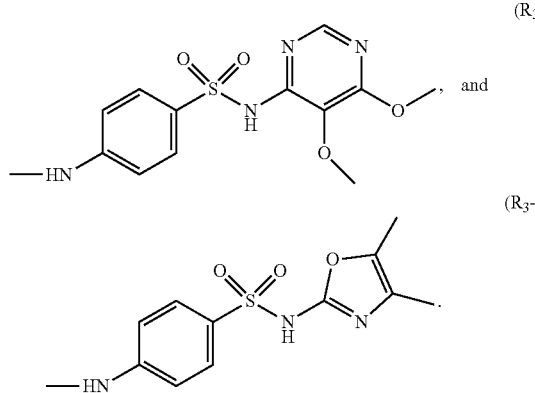

$R_5$ is selected from the group consisting of $NH_2$, NH-alkyl, NH-aryl, NH-heteroaryl, X, $NO_2$, and CN. R6 is selected from the group consisting of $NH_2$, NH-alkyl, NH-aryl, NH-heteroaryl, X, $NO_2$, CN, —$CH_2$Ph-substitued phenyl, and heteroaryl alkyl (C1-C17). X is a halogen. Exemplary embodiments may include a derivative of formula I or a pharmaceutical acceptable salt of formula I or of the derivative.

Exemplary embodiments may include a compound of formula (Ia)

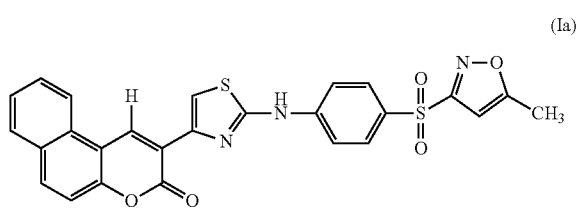 [SMILES: Cc1cc(S(=O)(=O)c2ccc(Nc3nc(-c4cc5c(ccc6ccccc65)oc4=O)cs3)cc2)no1]

Exemplary embodiments may include a compound having a derivative structure of formula (Ia) or pharmaceutical acceptable salt of formula (Ia) or the derivative structure.

The compound of formula (Ia) contains a benzocoumarin-thiazol moiety coupled with a well known antibacterial drug known as Sulfamethoxazole (4-Amino-N-(5-methylisoxazol-3-yl)-benzenesulfonamide) (also called SMZ or SMX) used for urinary tract infections, bronchitis, and prostatitis. It is successful against both gram negative bacteria like *Listeria monocytogenes* and positive bacteria for example *E. coli*. SMZ is mostly used in combination with trimethoprim (abbreviated SMX-TMP). The combination of these three important pharmacophores in a single structure leads to a very effective compound.

The compounds of invention contains all these useful pharmacophore in a single structural unit.

The benzene sulfonyl group may be replaced by the following:
Benzene sulfonamide, 5-chloro-8-quinolinefluoromethanesulfonate
1-(3-Cyanopropyl)-3-methylimidazolium bis(trifluoromethylsulfonyl)amide
(1R)-trans-N,N'-1,2-cyclohexanediylbis(1,1,1-trifluoromethanesulfonamide)
N-cyclohexyl-N'-(2-morpholinoethyl)carbodiimide methyl-p-toluenesulfonate
Cyclopropansulfonamide
3,5-Dichlorobenzenesulfonamide
2,3-Dichlorothiophene-5-sulfonamide
2,3-Dichlorothiophene-3-sulfonamide
2,4-Difluorobenzenesulfonamide
2,5-Difluorobenzenesulfonamide
2,6-Difluorobenzenesulfonamide
N-Ethyl-p-toluenesulfonamide
3-Fluorobenzenesulfonamide
5-Fluorobenzenesulfonamide
N-Fluorobenzenesulfonamide
3-Fluoro-4-methylbenzenesulfonamide
4-Fluoro-2-methylbenzenesulfonamide
N-(2-Fluorophenyl)methanesulfonamide
4-Methoxybenzenesulfonamide
2-Methyl-2-propanesulfinamide
(R)-(+)-2-Methyl-2-propanesulfinamide
3-Methyl-1-(3'-sulfoamidophenyl)-5-pyrazolone
3-Methyl-1-(4'-sulfoamidophenyl)-5-pyrazolone
N-(2-(Methyl sulfonyl)phenyl)acetamide
N-Methyl-p-toulenesulfonamide Apparatus, Reagents and Chemicals All commercial products were purchased from Sigma-Aldrich. Solvents used were of analytical grade and, when necessary, were purified and dried by the standard methods. Melting points were determined in open capillary tubes on a Stuart melting point apparatus. The infrared (IR) spectra were run on the single beam Nicolet IR 100 (Fourier-Transform (FT)) spectrophotometer; The proton nuclear magnetic resonance ('H-NMR) and carbon 13 NMR ($^{13}$C-NMR) spectra were recorded in deuterated-dimethyl sulfoxide (DMSO-$d_6$) using NMR Bruker DPX 300 spectrometer operating at 300 MHz. Tetramethylsilane (TMS) was used as internal standard with the deuterium signal of the solvent as the lock and chemical shifts δ recorded in part per minute (ppm). The elemental analysis (C, H, N, S) of the compounds were performed using Flash EA 1112 elemental analyzer. Compounds were routinely checked by thin layer chromatography (TLC) on silica gel G plates using eluting solvents, petroleum ether:ethyl acetate (7:3, v/v). Also, the developed plates were visualized using a ultra violet (UV) lamp for the presence of spots and $R_f$ values were duly calculated.

General Procedure for Synthesis

Scheme 1: Three Step Reaction

Step 1: Synthesis of 3-acetylcoumarins

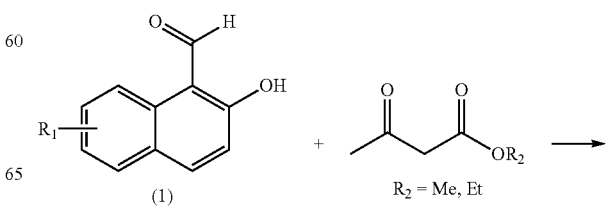

-continued

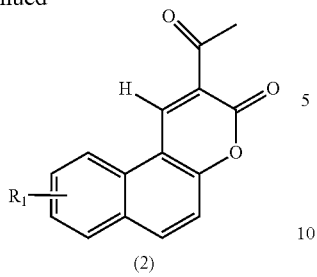

(2)

Step 2: Synthesis of 3-bromoacetylcoumarins

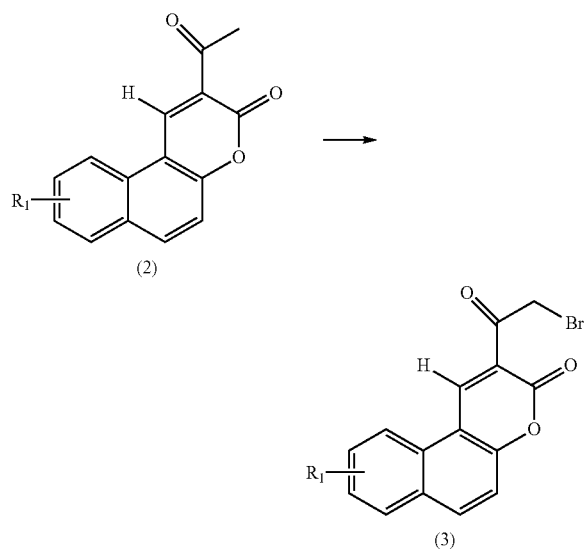

Step 3: In Situ Formation of Thiazole and Coupling with Sulfonamides

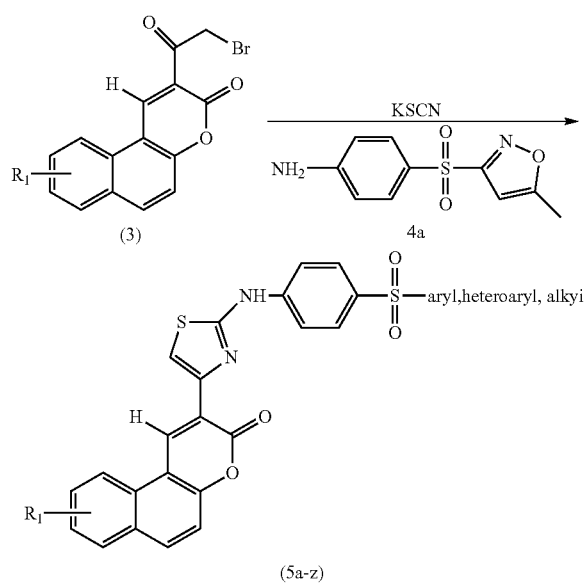

-continued

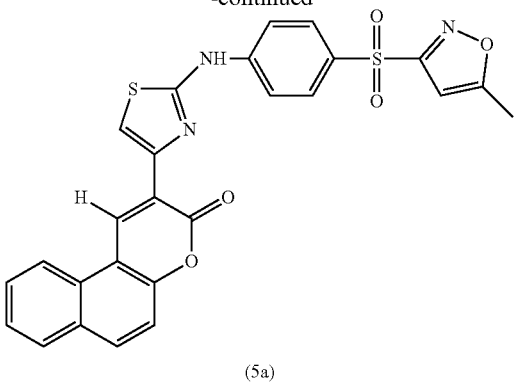

(5a)

specific structure of title compound
$R_1$ = HR═H, X, $NO_2$, CN, isomeric di-X, tri-X, isomeric di-$NO_2$, tri-X, isomeric di-OMe, tri-OMe, ismeric di-CN, tri-CN Step 1: Synthesis of 2-acetyl-3H-benzo[f]chromen-3-one (Compound 2)

To a cold stirred mixture of 2-hydroxy-1-naphthalaldehyde (Compound 1) (0.1 mmol) and ethyl acetoacetate (0.1 mmol, 12.63 ml) was added 0.01 mmol (1.12 ml) of piperidine by the rapid shaking. After 30 minutes, the solids that separated were filtered off and washed with ethanol. Crystallization of the solid from pure water gave pure 2-acetyl-3H-benzo[f]chromen-3-one (Compound 2).

The yield of this reaction was 88% with resulting compound having a melting point (m.p.) of 190° C. Using potassium bromide (KBr) as a diluent, the IR absorption peaks of the resulting compound were: Ar C—H 3065 $cm^{-1}$, C═O 1705 $cm^{-1}$, (lactone C═O) 1724 $cm^{-1}$, Ar C═C 1556 $cm^{-1}$, C—O—C 1228 $cm^{-1}$. These spectrum peaks and physical data correspond with compound 2.

Step 2: Synthesis of 2-(2-bromoacetyl)-3H-benzo[f] chromen-3-one (Compound 3)

A solution of bromine (0.01 mol, 1.72 g) in chloroform was added by rapidly shaking to a solution 2-acetyl-3H-benzo[f]chromen-3-one (Compound 2) (0.01 mol, 2.38) in chloroform. The mixture was heated under reflux for 2 hours and cooled. The solid separated was crystallized from chloroform-ethanol (2:1) to get pure 2-(2-bromoacetyl)-3H-benzo[f]chromen-3-one (Compound 3).

The yield of Step 2 is 81%. The melting point of the resultant compound is 184° C. Using KBr as a diluent, the IR absorption peaks Ar C—H 3044 $cm^{-1}$, C═O 1700 $cm^{-1}$, (lactone C═O) 1722 $cm^{-1}$, Ar C═C 1553 $cm^{-1}$, C—O—C 1238 $cm^{-1}$, and C—Br 582 $cm^{-1}$. This physical and spectroscopic data is in accordance with structure of Compound 3.

Step 3: Synthesis of 2-(2-(4-(5-methylisoxazol-3-ylsulfonyl)phenylamino)thiazol-4-yl)-3H-benzo[f] chromen-3-one (Compound 5)

To a stirred solution of the 2-(2-bromoacetyl)-3H-benzo [f]chromen-3-one (Compound 3) (0.001 mol) in 30 mL of ethanol in a round bottom flask fitted with a reflux condenser, (0.001 mol) of KSCN was added in small portions. The reaction mixture was stirred further at 45-50° C. for one hour, and 4-((5-methylisoxazol-3-yl)sulfonyl)aniline) (Sulfamethoxazole) (Compound 4) (0.0012 mol) was added. The reaction mixture was refluxed for 5 hours. The solid product obtained by pouring the reaction mixture into ice-cold water. The solid separated was purified by recrystallization from ethanol to create 2-(2-(4-(5-methylisoxazol-3-ylsulfonyl) phenylamino)thiazol-4-yl)-3H-benzo[f]chromen-3-one (Compound 5).

TABLE 1

| Physical and Spectroscopic Data of Reaction Results for Compound 5 | |
|---|---|
| Appearance | Yellow Solid |
| Yield | 62% |
| Melting Point | 255° C. |
| Response Factor (Rf) | 0.53 (Pet Ether:Ethyl Acetate 7:3) |
| Fourier Transform infrared spectroscopy (FTIR) (KBr): N—H | 3358 cm$^{-1}$ |
| FTIR (KBR): C═O | 1729 cm$^{-1}$ |
| FTIR (KBR): CH Strech-ing | 3071 cm$^{-1}$, 2982$^{-1}$, 2920 cm$^{-1}$ |
| FTIR (KBR): C═N str | 1534 cm$^{-1}$ |
| FTIR (KBR): C═C str | 1495 cm$^{-1}$ |
| 1H NMR (300 MHz, dimethyl sulfoxide (DMSO)-d6): s, 3H CH3 | 2.212 ppm |
| 1H NMR (300 MHz, DMSO-d6): s, 3H CH3 (s, 1H, (s, 1H, C—H isoxazolering) | 6.03 ppm |
| 1H NMR (300 MHz, DMSO-d6): s, 1H, CH | 7.23 ppm |
| 1H NMR (300 MHz, DMSO-d6): m, 6H, Ar—H | 7.24-8.26 ppm |
| 1H NMR (300 MHz, DMSO-d6): d, 2H, J = 7.60 Hz Ar—H | 7.56 ppm |
| 1H NMR (300 MHz, DMSO-d6): d, 2H, J = 7.7 Hz Ar—H | 7.01 ppm |
| 1H NMR (300 MHz, DMSO-d6): s, 1H, benzocoumarin H-4 | 9.03 ppm |
| 1H NMR (300 MHz, DMSO-d6): s, 1H, NH | 12.05 ppm |
| 13C-NMR (75 MHz, DMSO-d6): C═O | 169.3 ppm |
| 13C-NMR (75 MHz, DMSO-d6): C═N | 160.18 ppm, 156.6 ppm |
| 13C-NMR (75 MHz, DMSO-d6): C═C | 155.2 ppm |
| 13C-NMR (75 MHz, DMSO-d6): Ar—C | 169.5 ppm, 153.8 ppm, 146.8 ppm, 145.8 ppm, 138.6 ppm, 135.6 ppm, 134.6 ppm, 133.4 ppm, 131.6 ppm, 130.4 ppm, 129.5 ppm, 129.3 ppm, 128.6 ppm, 127.6 ppm, 123.7 ppm, 122.7 ppm, 121.2 ppm, 116.9 ppm, 114.8 ppm, 109.5 ppm |
| 13C-NMR (75 MHz, DMSO-d6): C—C | 100 ppm |
| 13C-NMR (75 MHz, DMSO-d6): CH3 | 12.9 ppm |
| Analytical Calculated (Anal. Calcd.) for C23H17N3O5S2 | C, 60.57; H, 3.32; N, 8.15; S, 12.44 |
| Found: | C, 60.55; H, 3.34; N, 8.19; S, 12.51 Electron Ionization Mass Spectrometry (EIMS): 515 mass to charge ratio (m/z) |

Scheme 2: Modified Three Step Reaction

Step 1: Synthesis of 3-acetylcoumarins

Step 2: Synthesis of 3-bromoacetylcoumarins

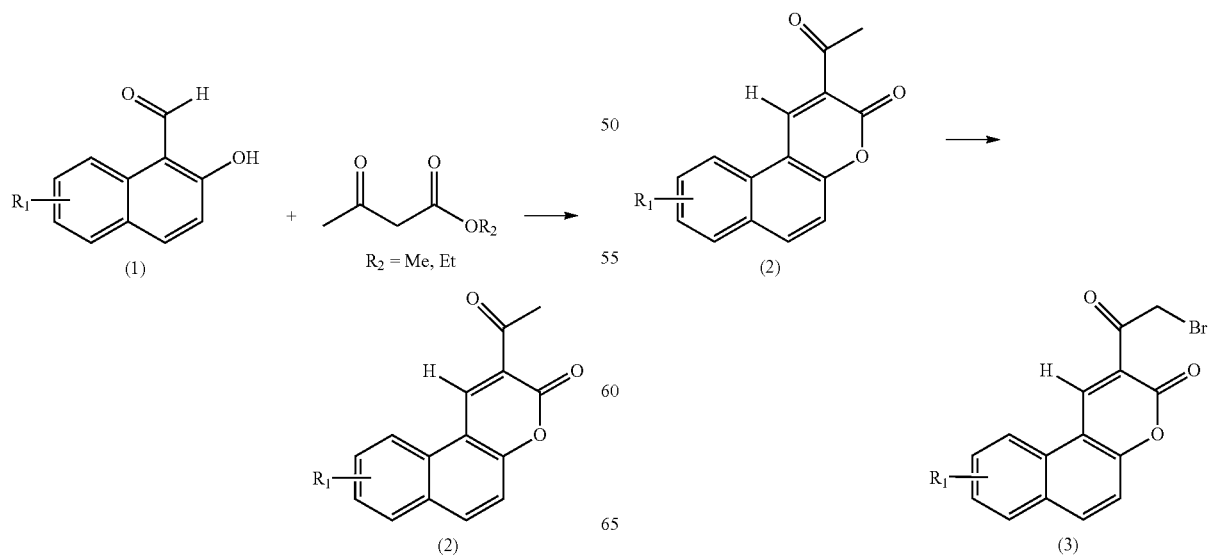

Step 3: Concurrent Thiazole Formation and Coupling with Sulfonamides

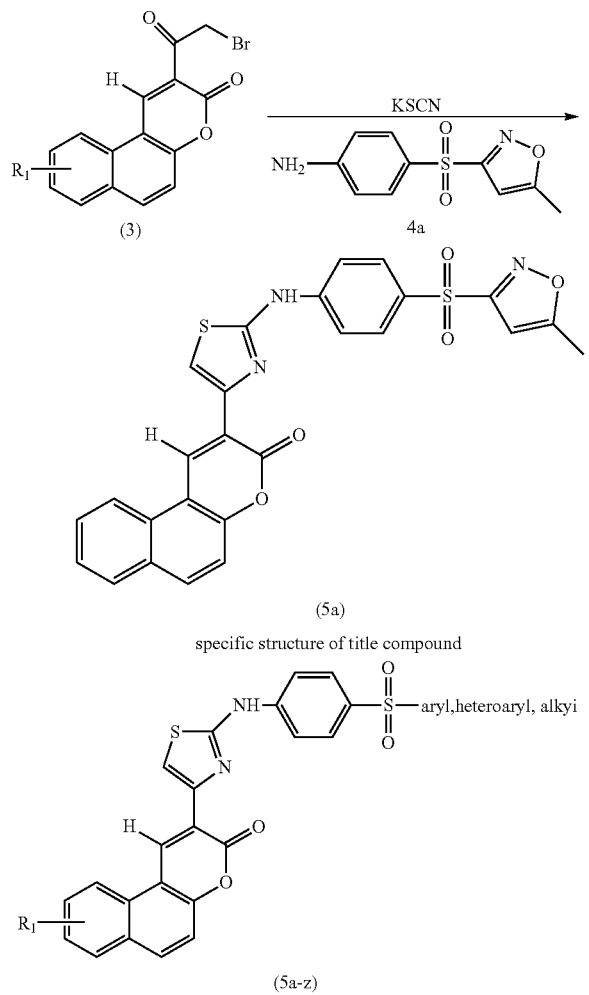

$R_1$ = HR ═ H, X, $NO_2$, CN, isomeric di-X, tri-X, isomeric di-$NO_2$, tri-X, isomeric di-OMe, tri-OMe, ismeric di-CN, tri-CN Scheme 2 above shows an alternative reaction path that is identical to Scheme 1, except that Scheme 2 utilized concurrent thiazole formation instead of in situ formation of thiazole.

Results and Discussion:

Synthesis of Coumarinyl Derivative (5)

These derivatives have been synthesized to obtain coumarins-thiazole-sulofonamide conjugates potentially applicable as drugs and bioimaging materials.

Coumarinyl derivative (5) have been synthesized well in excellent yields and high purity through multistep accessible route following the scheme 1. The coumarin ring (2) was synthesized using naphthaldehyde (1) and ethyl acetoacetate. Bromination at alpha position of 3-acetylcoumarin provided the brominated coumarin (3). The title compound (5) was obtained by reacting the brominated coumarin (3) with KSCN and substituted anilines (4) at reflux. The completion of the reaction was monitored by the TLC of reaction mixture. Purified by recrystallization from ethanol to afford 5.

The FTIR spectra of coumarin-thiazole-sulfonyl conjugate (5) exhibited absorption bands due to N—H, Ar—H, C═O of lactone, C═N of imine, C═C, C═S and C—O, stretchings and bending vibrations at 3370-3399, 2980-3170, 1727-1749, 1620-1652, 1510-1533, 1411-1431, 1280-1295, 1105-1155, 836-860, and 793-818 $cm^1$ respectively. In the case of coumarin 5d, ester motif was confirmed by the appearance of a peak at 1727 due to the carbonyl group of cyclic six membered esters. Presence of peak at 1149 $cm^{-re}$ was a result of C—OC. The absorptions at 1630, 1533 and 859 $cm^{-he}$ depicted the presence of C═C stretching and bending vibrations respectively. FTIR spectrum of 5, showed NH group peak at 3380 $cm^{-1}$ and C═C—H stretching vibrations at 3168 $cm^{-n}$. The $^1$H-NMR spectrum of compound 5 showed 6H singlet at 2.21 ppm and 3H singlet at 2.39 ppm due to three substituents attached to benzene. Singlet peak at 11.92 ppm is assigned to N—H substituted by heterocyclic and phenyl rings of coumarin. The multiplets at 7.32-8.44 ppm are due to six mutually coupled aromatic protons attached to coumarin part of the molecule. The distinguishing peak for all coumarins is the presence of coumarin H-4 at 9.33 ppm. The difference between 5 series is due to condensed substituted aromatic moieties. The $^{113}$C-NMR spectra of 5a showed peaks for different carbon atoms present within the molecule The carbonyl and imine carbons were observed are at 169.3 and 159.1 ppm respectively. Three methyl carbons at benzene ring in 5a appeared at 21.5 and 18.2 ppm. Similarly the rest of compounds 5 were confirmed by $^1$H-NMR and $^{13}$C-NMR spectra.

Synthesis

Coumarinyl derivatives 5a-j have been synthesized well in excellent yields and high purity through synthetic route depicted in scheme 1. These derivatives were synthesized in order to obtain coumarin derivatives potentially applicable as drugs and bioimaging materials. Thus, coumarins derivatives (1) were synthesized by reacting naphthaldehyde and ethyl acetoacetate which are further brominated at alpha-position to create (2). Cyclocondensation of alpha-bromo intermediate with different sulfonamide derivatives 4a-j in presence of potassium thiocyanate at reflux afforded the in situ formation of thiazole ring followed by the attachment of sulfonamide moiety in a single step (scheme 1).

What is claimed is:
1. A compound having a structure of formula (I):

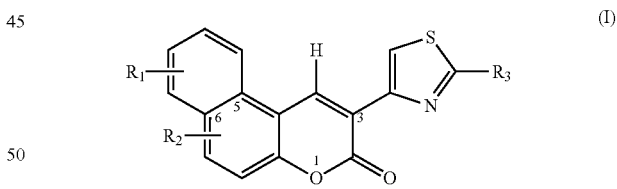

wherein:
$R_1$ is selected from the group consisting of H, alkyl (C1-C17), X, $NO_2$, and CN;
$R_2$ is selected from the group consisting of H, alkyl (C1-C17), X, $NO_2$, and CN;
$R_3$ is selected from the group consisting of:

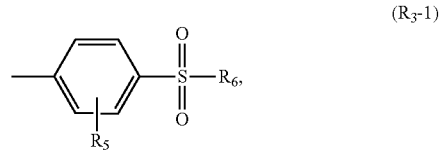

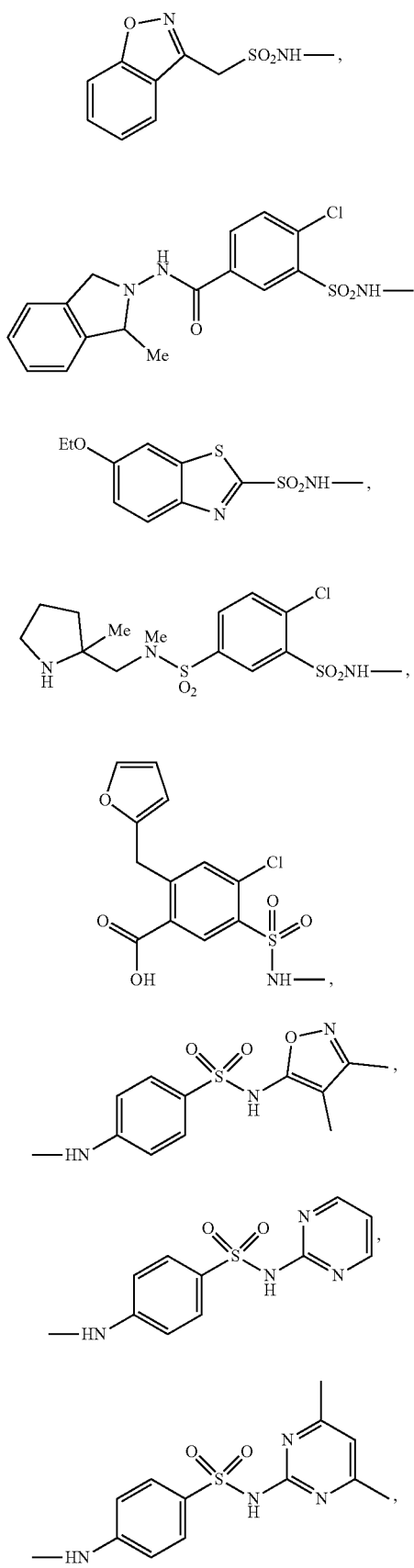

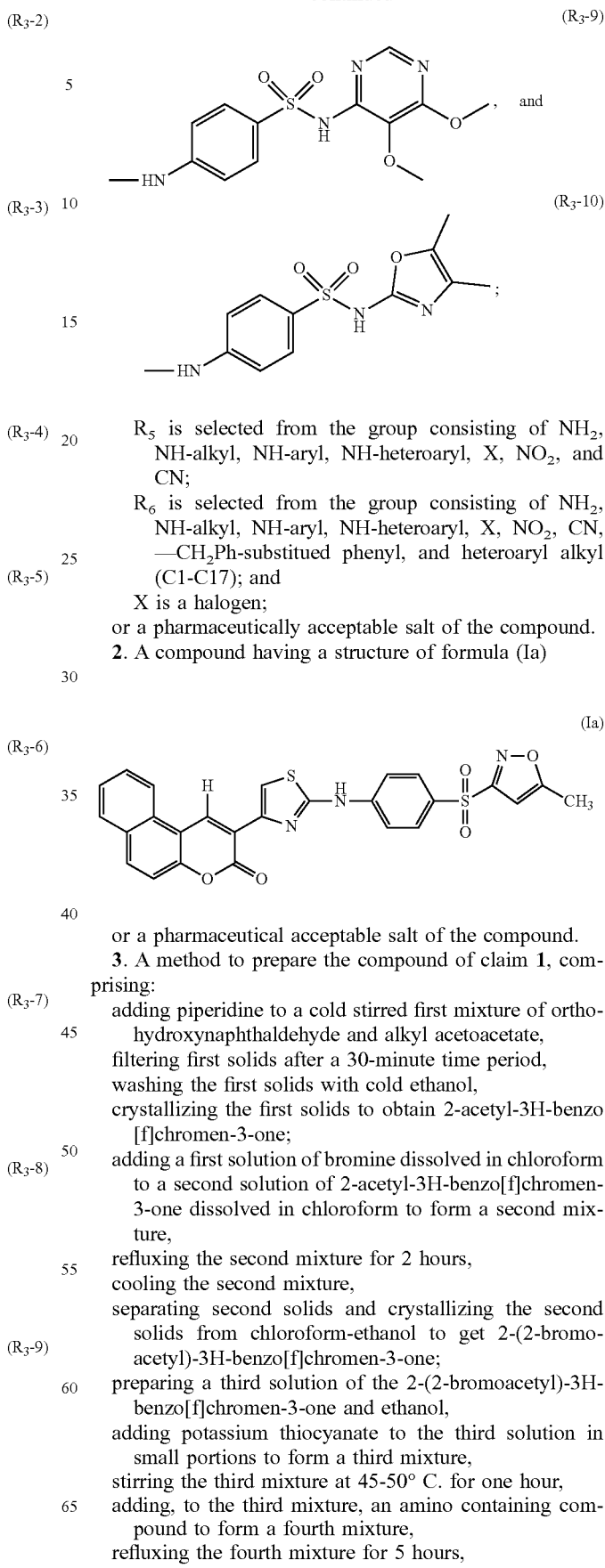

R₅ is selected from the group consisting of $NH_2$, NH-alkyl, NH-aryl, NH-heteroaryl, X, $NO_2$, and CN;

R₆ is selected from the group consisting of $NH_2$, NH-alkyl, NH-aryl, NH-heteroaryl, X, $NO_2$, CN, —$CH_2$Ph-substitued phenyl, and heteroaryl alkyl (C1-C17); and X is a halogen;

or a pharmaceutically acceptable salt of the compound.

2. A compound having a structure of formula (Ia)

or a pharmaceutical acceptable salt of the compound.

3. A method to prepare the compound of claim 1, comprising:
adding piperidine to a cold stirred first mixture of ortho-hydroxynaphthaldehyde and alkyl acetoacetate,
filtering first solids after a 30-minute time period,
washing the first solids with cold ethanol,
crystallizing the first solids to obtain 2-acetyl-3H-benzo[f]chromen-3-one;
adding a first solution of bromine dissolved in chloroform to a second solution of 2-acetyl-3H-benzo[f]chromen-3-one dissolved in chloroform to form a second mixture,
refluxing the second mixture for 2 hours,
cooling the second mixture,
separating second solids and crystallizing the second solids from chloroform-ethanol to get 2-(2-bromo-acetyl)-3H-benzo[f]chromen-3-one;
preparing a third solution of the 2-(2-bromoacetyl)-3H-benzo[f]chromen-3-one and ethanol,
adding potassium thiocyanate to the third solution in small portions to form a third mixture,
stirring the third mixture at 45-50° C. for one hour,
adding, to the third mixture, an amino containing compound to form a fourth mixture,
refluxing the fourth mixture for 5 hours, pouring the fourth mixture into ice-cold water to separate third solids,
purifying the third solids by recrystallization from ethanol to obtain a compound having a structure of formula (I):

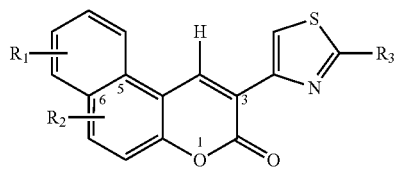
(I)

wherein:
R₁ is selected from the group consisting of H, alkyl (C1-C17), X, NO₂, and CN;
R₂ is selected from the group consisting of H, alkyl (C1-C17), X, NO₂, and CN;
R₃ is selected from the group consisting of:

(R₃-1)

(R₃-2)

(R₃-3)

(R₃-4)

(R₃-5)

(R₃-6)

(R₃-7)
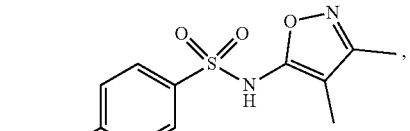

(R₃-8)
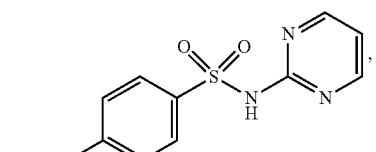

(R₃-9)
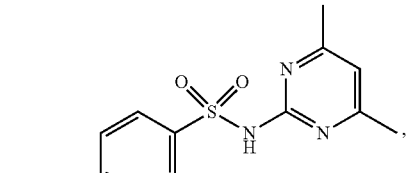

(R₃-9)
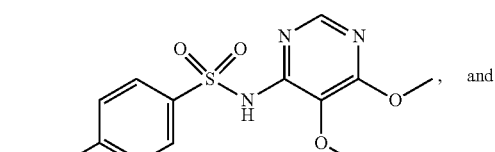
and (R₃-10)
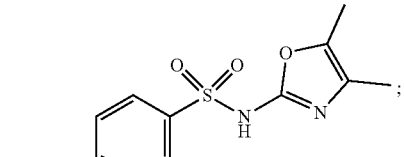

R₅ is selected from the group consisting of NH₂, NH-alkyl, NH-aryl, NH-heteroaryl, X, NO₂, and CN;
R₆ is selected from the group consisting of NH₂, NH-alkyl, NH-aryl, NH-heteroaryl, X, NO₂, CN, —CH₂Ph-substitued phenyl, and heteroaryl alkyl (C1-C17); and
X is a halogen.

4. A method of preparing the compound of claim 2, comprising:
preparing a first mixture of 2-hydroxy-1-naphthaldehyde and ethyl acetoacetate,
adding piperidine to the cold stirred first mixture,
filtering first solids after a 30-minute time period,
washing the first solids with ethanol,
crystallizing the first solids from pure water to get 2-acetyl-3H-benzo[f]chromen-3-one;
adding a first solution of bromine and chloroform into a second solution of 2-acetyl-3H-benzo[f]chromen-3-one and chloroform to form a second mixture,
heating the second mixture under reflux for 2 hours,
cooling the second mixture,
separating second solids and crystallizing from chloroform-ethanol to get pure 2-(2-bromoacetyl)-3H-benzo[f]chromen-3-one;

preparing a third solution of the 2-(2-bromoacetyl)-3H-benzo[f]chromen-3-one in ethanol, adding potassium thiocyanate to the third solution in small portions to form a third mixture, stirring the third mixture 45-50° C. for one hour, adding 4-((5-methylisoxazol-3-yl)sulfonyl)aniline) (Sulfamethoxazole) to the third mixture to form a fourth mixture, refluxing the fourth mixture for 5 hours, pouring the fourth mixture into ice-cold water to get third solids, purifying the third solids by recrystallization from ethanol to obtain the compound of formula (Ia).

5. A pharmaceutical composition comprising a therapeutically effective amount of the compound of claim 1, or a pharmaceutically acceptable salt of the compound and a pharmaceutically acceptable carrier.

6. A pharmaceutical composition comprising a therapeutically effective amount of the compound of claim 2 and a pharmaceutically acceptable carrier.

\* \* \* \* \*